(12) United States Patent
Dorsey et al.

(10) Patent No.: US 8,129,149 B1
(45) Date of Patent: Mar. 6, 2012

(54) RAPID AND SENSITIVE METHOD TO MEASURE ENDONUCLEASE ACTIVITY

(75) Inventors: Russell M. Dorsey, Fallston, MD (US); Robert W. Dorsey, Middle River, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 232 days.

(21) Appl. No.: 12/269,448

(22) Filed: Nov. 12, 2008

(51) Int. Cl.
*C12P 19/34* (2006.01)

(52) U.S. Cl. ..................................... 435/91.2

(58) Field of Classification Search ..................... None
See application file for complete search history.

(56) References Cited

U.S. PATENT DOCUMENTS 7,252,940 B2    8/2007   Kutyavin et al. ................. 435/6
7,435,561 B2 * 10/2008   Piepenburg et al. ......... 435/91.2

OTHER PUBLICATIONS

Freisinger et al., Lesion (in)tolerance reveals insights into DNA replication fidelity, The EMBO Journal (2004) 23, 1494-1505.*
Mol et al., DNA-bound structures and mutants reveal abasic DNA binding by APE1 DNA repair and coordination, Nature |vol. 403 | Jan. 27, 2000, pp. 451-456.*
Buck et al., Design Strategies and Performance of Custom DNA Sequencing Primers, BioTechniques 27:528-536 (Sep. 1999).*

* cited by examiner

*Primary Examiner* — Mark Staples
(74) *Attorney, Agent, or Firm* — Ulysses John Biffoni

(57) ABSTRACT

A rapid and sensitive method to measure endonuclease activity comprising reacting a substrate suspected of having endonuclease activity with a synthetic nucleotide to induce endonuclease cleavage of the synthetic nucleotide followed by measurement of activity by carrying out a polymerase chain reaction (PCR). When no polymerase chain reaction takes place when carrying out the method it is indicative of no endonuclease activity in the substrate. Synthetic oligonucleotides, primers, and probes useful for carrying out the method are disclosed.

2 Claims, 4 Drawing Sheets

Introduction of Synthetic Nucleotide Containing an Apurinic/Apyrimidinic Site to
Endonuclease, Followed by Endonuclease Hydrolysis at Site Could have nucleotide hybridize completely and use a modified 3' end block extension Figures 1 and 2. Endonuclease is introduced to synthetic nucleotide to cleave the phosphodiester backbone.

Extension of the 3' End of the Nucleotide Substrate

Endonuclease Hydrolyzed Substrate

Extend 5' (labeled A) with DNA polymerase; B is destroyed by 5' to 3' exonuclease activity of DNA polymerase Figures 3 and 4. Degradation of the 5' end of endonuclease substrate and extension of the 3' end the length of the DNA.

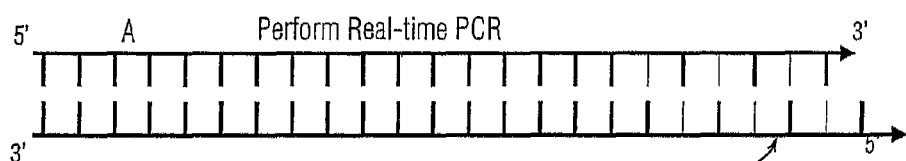
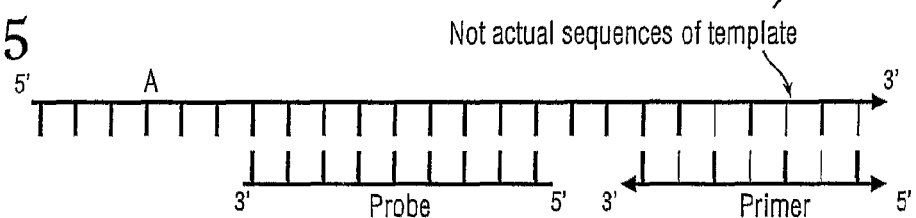
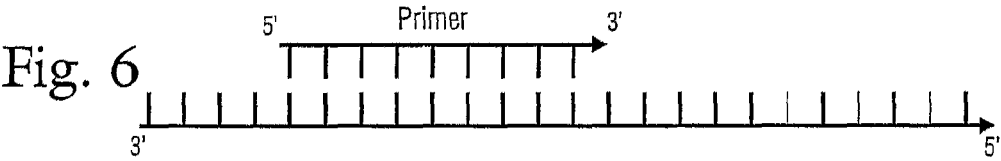
Figures 5 and 6. Real-time PCR to detect the initial endonuclease action on the substrate.

Figure 7. Oligonucleotide synthesized with an abasic site (Well A04) is cleaved by APE and amplified through PCR.

RAPID AND SENSITIVE METHOD TO MEASURE ENDONUCLEASE ACTIVITY

GOVERNMENT INTEREST

The invention described herein may be manufactured, used and licensed by or for the U.S. Government.

FIELD OF THE INVENTION

The herein disclosed invention finds applicability in the field of bioassay or biotesting, and specifically in the field where endonuclease activity is to be detected and measured.

BACKGROUND OF THE INVENTION

An endonuclease is an enzyme that catalyzes the hydrolysis of phosphodiester linkages within a nucleotide chain. Endonucleases have been widely used for the creation of recombinant DNA molecules, mapping mutations and for studying the interactions of DNA with various intercalating agents. Certain types of endonucleases are highly selective for a specific nucleic acid recognition sequence or for a single-stranded region within double-stranded nucleic acid.

Nucleases are critical to the successful execution of nearly all DNA damage responses. In particular, these enzymes recognize and excise specific forms of genetic damage, or minimally, initiate removal of a lesion-containing DNA strand. As damage excision is essential for the maintenance of genetic integrity for cells to include bacterial and neoplastic cells, altering the activity of Apurinic/Apyrimidinic endonuclease (APE) could hold promise for enhanced or novel treatments to infection and cancer.

The utility of single-strand-specific nucleases as analytical tools has been widely recognized and has led to their extensive application as probes for the determination of nucleic acid structure. The technology described in this invention will not only dramatically increase the sensitivity of quantitating endonuclease activity, but will duly allow for enzyme substrate characterization.

PRIOR ART REFERENCES

Kutyavin et al—U.S. Pat. No. 7,252,940 is directed to an abasic site endonuclease assay. The assay of this invention differs from that of Kutyavin et al in that APE cleavage of the abasic DNA allows for subsequent PCR amplification which makes the assay of this invention more sensitive than the endonuclease assay of Kutyavin et al where APE cleavage of the DNA molecule merely releases a fluorophore from a quencher dye.

DEFINITION OF CERTAIN ABBREVIATIONS AS USED IN THIS INVENTION

APE is an endonuclease which is able to cleave Apurinic/Apyrimidinic site contained in a nucleotide.

PCR—polymerase chain reaction.

Taq polymerase—heat stable polymerase isolated from bacterium *Thermus acquaticus*.

OBJECTS OF THE INVENTION

The herein disclosed invention has a main object of providing a rapid and sensitive method for measuring endonuclease activity.

This and other objects of the present invention will become apparent from a reading of the following specification taken in conjunction with the enclosed drawings.

BRIEF SUMMARY OF THE INVENTION

Design of Target Molecule

In the proposed method a nucleotide substrate (target molecule) will be synthesized to contain specific hydrolysis site for the endonuclease of interest. The target molecule will be double-stranded with the exception of a single-stranded hydrolysis site. Additionally, the target molecule will be engineered to be non-complementary at the 3'-end. The role of the non-complementary sequence at the 3'-end in this method will be to prevent DNA polymerase extension. To ensure the prevention of the polymerase extension, the 3'-end of the target molecule may be further modified.

Overview of the Invention

The inventors have demonstrated that DNA polymerase and PCR can be employed to identify APE activity on a synthetic DNA oligonucleotide that contains an Apurinic/Apyrimidinic site. Their approach utilizes a synthetic DNA oligonucleotide to serve as a substrate for APE, which contains an internal tetrahydrofuran (an abasic site analog), and a 3' terminal dideoxy C (3' hydroxyl group) to prevent extension by DNA polymerase until APE hydrolyzes the oligonucleotide. The sequences for both the substrate and the template were designed for this experiment and were all synthetic; the sequences could easily be varied. This not only allows for future studies of the APE's interaction with the abasic site containing substrate, but also the interaction of APE with the complementary duplex DNA. Amplification and detection of the substrate nucleotide is carried out via Taq polymerase and real-time PCR.

BRIEF DESCRIPTION OF THE DRAWINGS

FIGS. 1-6 schematically show a method of this invention by which endonuclease activity of a substrate is measured using a DNA target molecule. The method provides a rapid and sensitive means for measuring endonuclease activity.

Figure 1:
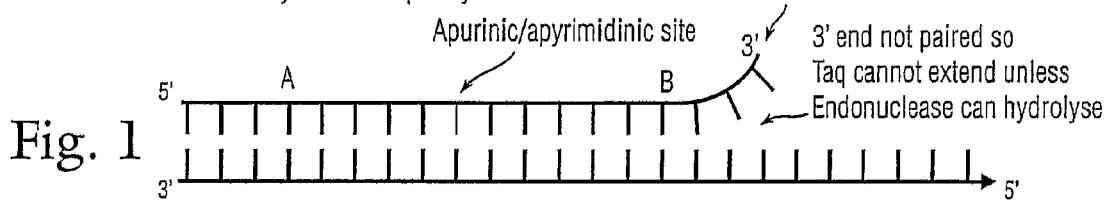
Figure 2:
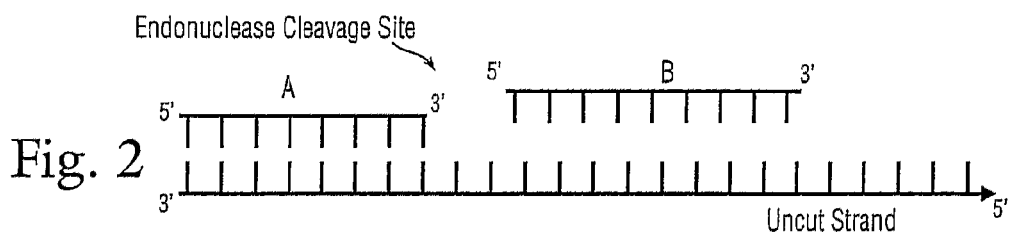

When the DNA target molecule is introduced to the endonuclease it will catalyze the site specific hydrolysis of the phosphodiester backbone (FIGS. 1 and 2). Following hydrolysis, DNA polymerase with 5'→3' exonuclease activity is added. The DNA polymerase will catalyze the extension of the 3' end of the cut DNA strand. The polymerase will also hydrolyze the cut strand in the region downstream of the endonuclease cleavage (portion B, FIG. 2). After the cut strand has been extended along the entire length of the uncut strand, a template molecule for PCR will have been generated. A quantitative PCR assay will be performed to determine the amount of cleavage of the endonuclease enzyme (FIGS. 5 and 6).

With particular reference to FIGS. 1 and 2 there is described the introduction of a synthetic nucleotide containing an apurinic/apyrimidinic site to endonuclease followed by endonuclease hydrolysis at the site. More particularly with reference to FIGS. 1 and 2 there is schematically shown the method of this invention involving the introduction of an endonuclease to a synthetic nucleotide containing an apurinic/apyrimidinic site in order to cleave the phosphodiester backbone.

Note particularly in FIG. 1 the arrow directed to the Apurinic/Apyrimidinic site which is to be cleaved; and in FIG. 2 note the site has been cleaved into strands A and B.

Figure 3:
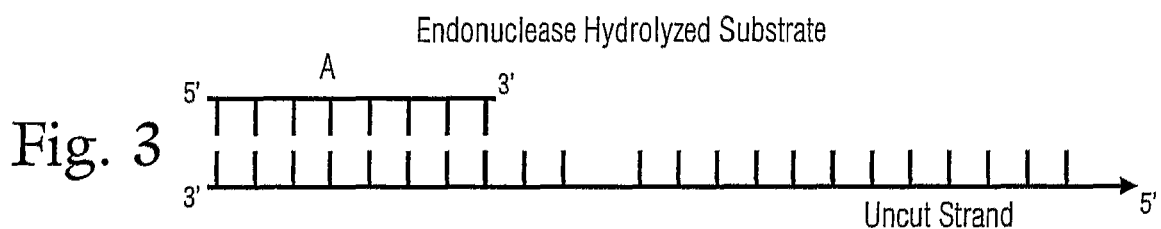
Figure 4:
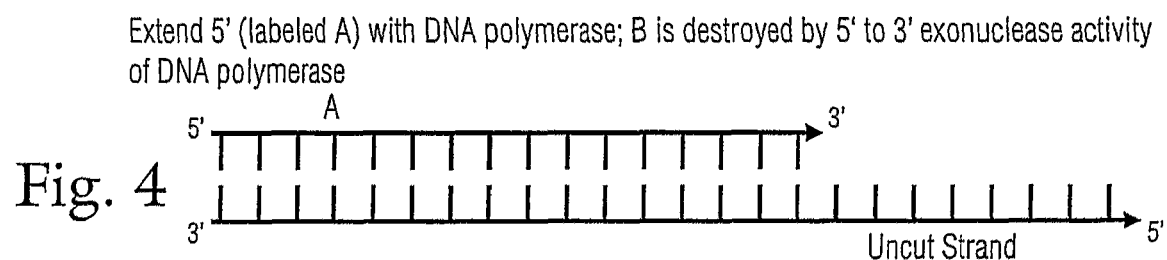

FIGS. 3 and 4 describe the extension of the 3' end of the nucleotide substrate. Specifically shown in FIGS. 3 and 4 is the degradation of the 5' end of the endonuclease substrate and extension of the 3' end the length of the DNA.

With particular reference to FIGS. 2 and 4 segment B is destroyed by 5' to 3' exonuclease activity of DNA polymerase; and segment A is extended with DNA polymerase.

FIGS. 5 and 6 are schematic representations of a PCR (polymerase chain reaction) presented in real-time to detect the initial endonuclease action on the substrate. PCR is performed and endonuclease activity is detected by virtue of there being a polymerase chain reaction; the fact of no polymerase chain reaction would be indicative of there being no endonuclease activity.

Figure 7:
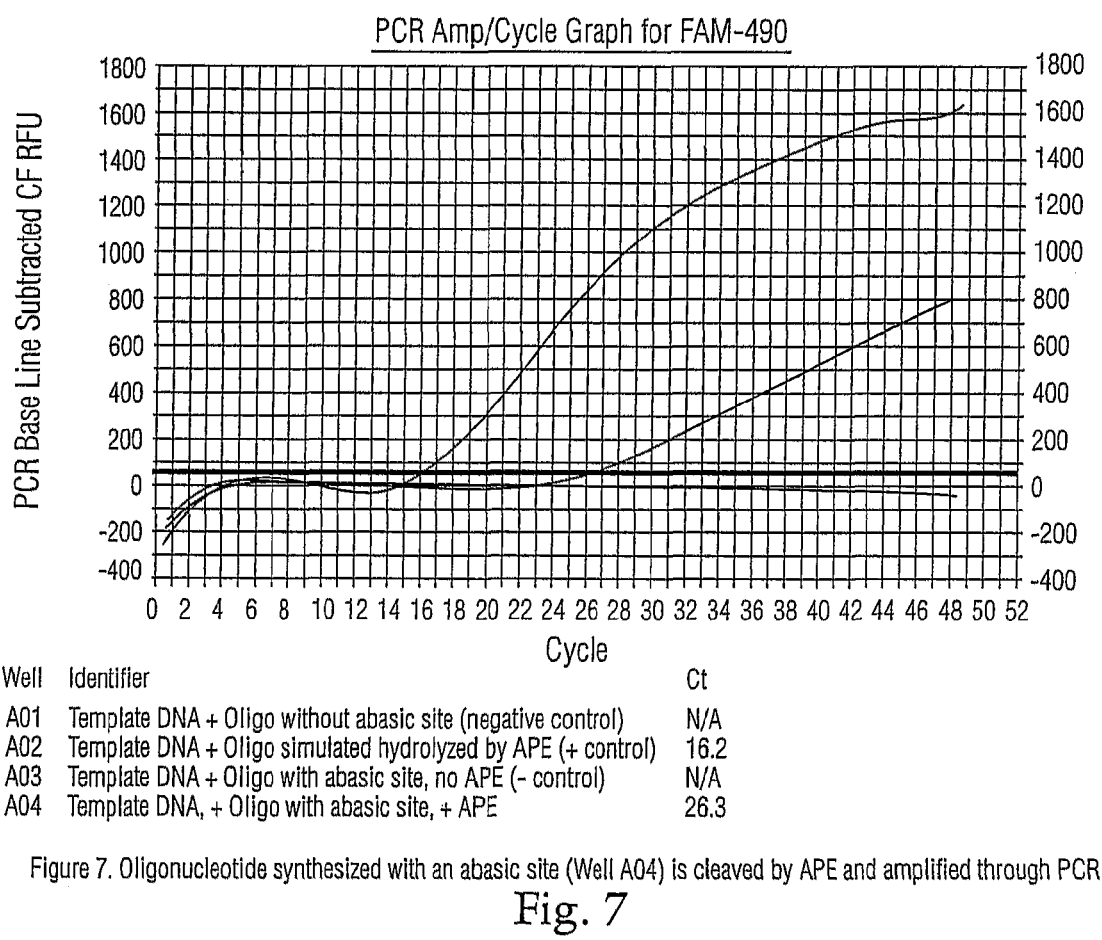

FIG. 7 is a graph showing oligonucleotide synthesized with an abasic site (Well A04) is cleaved by APE and amplified through PCR. The figure contains the amplification plots from a run that illustrates the function of the APE assay: well A01 was a negative control that contained Template DNA along with Substrate DNA that did not have an abasic site incorporated. This was not cut by APE and did not amplify by PCR; well A02 was a positive control that contained Template DNA combined with Substrate DNA that was simulated to have been cut by APE, this amplified with a CT of 16.2; well A03 was a negative control that contained the abasic Substrate DNA and Template DNA without the addition of APE, no amplification took place; well A04 contained abasic Substrate DNA and Template DNA with APE, this amplified with a CT of 26.3.

DESCRIPTION OF THE INVENTION

Materials and Methods
Enzymes, Chemicals and Oligonucleotides

Recombinant APE1 at 10,000 units/ml in 50% glycerol was purchased from NEW ENGLAND BIOLABS. One unit is defined as the amount of enzyme required to hydrolyze 20 pmol of a 34 bp oligonucleotide duplex containing a single AP site in a 10 ul reaction volume over one hour at 37° C. The reaction buffer consisted of 50 mM potassium acetate, 20 mM Tris-acetate, 10 mM magnesium acetate (pH 7.9) and 1 mM dithiothreitol.

All oligonucleotides, primers and probes were purchased from GENE LINK, INC. (Hawthorne, N.Y.). The two oligonucleotides that are specific to this technique, are designated the substrate and the template. The oligonucleotide with sequence 5'-GGGGTTTTGG GTTTTTTTAA TTTTAG-GTTG TGGTTGTGGT TGTCGGXGAC GTGTTGGTTT TT/3ddC/3' (SEQ. ID No. 1) serving as the substrate for APE contains the tetrahydrofuran, an abasic analog (X), and a 3' dideoxy-C to prevent extension by DNA polymerase. The oligonucleotide with sequence 5'-CATTTCGACC TAC-GATACGC GATCCAGTGT TTGTATGGAT CCT-GAGTTTT TCCAACACGT CTCCGACAAC CACAAC-CACA ACCATTTT/3ddC/3' (SEQ. ID. No. 2) referred to as the template contains a region complementary to the substrate oligonucleotide to form the double strand region required by APE. Forward primer, reverse primer, and probe have sequences respectively as follows: 5'-GGGGTTTTGG GTTTTTTTAA TTTTA-3' (SEQ. ID. No. 3); 5'-CATTTC-GACC TACGATACGC-3' (SEQ. ID No. 4); and 5'-FAM-TCCAGTGTTT GTATGGATCC TGAGT-TAMRA-3' (SEQ. ID No. 5). All oligonucleotides were purified by polyacrylamide gel electrophoresis before use. To minimize the possibility of the synthetic substrate exhibiting secondary structures, computational software was utilized during the design to determine oligonucleotide molecular weight, melting temperature, estimated absorbance coefficients, inter-molecular self-complementarily estimation and intra-molecular hairpin loop formation (http://www.basic.northwestern.edu/biotools/oligocalc.html http://www.idtdna.com/analyzer/Applications/OligoAnalyzer/Default.aspx).

The sequence of the bases are not shown complementary in order to prevent Taq polymerase from extending the substrate DNA until the APE cuts the substrate DNA. Said another way the strands are complementary, except for the 3' end of the substrate; and was designed with a 3ddC/3' block and is non-complementary to prevent Taq polymerase from extending the substrate molecule until it is cut by the APE.

APE Activity Technique

To perform the APE activity assay, 1 ul of 100 uM substrate oligonucleotide was hybridized to 1 ul of 100 pM template oligonucleotide by briefly vortexing at room temperature. To this, 1 U of APE1, 1 ul of 10× reaction buffer and 6 ul of molecular grade water were added. The reaction mixture was incubated for 1 hour at 37° C. then a 5 ul aliquot was added to the PCR reaction mixture consisting of 12.5 ul Bio-Rad master mix, 1 ul forward primer, 1 ul reverse primer, 1 ul probe, and 4.5 ul water.

After determining that the substrate and the template oligonucleotides efficiently hybridize to one another, the reagents where cycled separately and in combination without addition of APE to ensure that false amplification would not occur. The final two reaction conditions contained a substrate oligonucleotide referred to as "cut substrate". This oligonucleotide was designed to simulate a DNA substrate oligonucleotide that had been hydrolyzed by APE. The cut substrate demonstrated that once the 3' hydroxly block was liberated, DNA polymerase could extend the substrate molecule to allow PCR amplification to proceed (FIG. 5). Post-run polyacrylamide gel electrophoresis was performed to confirm florescence data from the real-time probe hydrolysis.

Real-Time PCR

Real-time PCR was performed using a BIO-RAD LABORATORIES (Hercules, Calif.) ICYCLER using BIO-RAD LABORATORIES IQTM SUPERMIX. Cycle times were an initial step at 95° C. for 10 minutes followed by an amplification program of 50 cycles of 3 seconds at 95° C., 5 seconds at 61° C., and 20 seconds at 72° C. with fluorescence acquisition in relative florescent units at the end of each extension. Melt curves were performed following amplification by utilizing BIO-RAD LABORATORIES IQTM SYBR GREEN SUPERMIX and a protocol with a 1 minute melt at 95° C. and 0.5° C. steps to 65° C. with 10 second dwell times.

The invention can be described as a method for the rapid and sensitive measurement of endonuclease activity comprising the steps of:

(a) reacting a substrate suspected as having endonuclease activity with a synthetic nucleotide containing an apurinic/apyrimidinic site to thereby subject the apurinic/apyrimidinic site to endonuclease hydrolysis, said hydrolysis producing a 5'→3' chain labeled A and a 5'→3' chain labeled B and leaving the complementary 3'→5' chain uncut;

(b) reacting the 5'→3' chain labeled A with DNA polymerase to form a complementary strand to the uncut strand 3'→5' of the chain; and (c) subjecting the reaction product of step (b) to a polymerase chain reaction to detect the initial endonuclease activity on said substrate.

An alternative description involves a method for the rapid and sensitive measurement of endonuclease activity comprising:

(a) reacting a synthetic DNA oligonucleotide with a substrate suspected of having APE endonuclease activity, said synthetic DNA oligonucleotide containing an internal tetrahydrofuran as an abasic site analog and a 3' terminal dideoxy C (3' hydroxyl group) to prevent extension by the DNA polymerase until the APE endonuclease hydrolyzes the oligonucleotide; and (b) reacting the hydrolyzed oligonucleotide for amplification and detection by Taq polymerase and real-time PCR to detect endonuclease activity in said substrate.

A further description of the invention calls for a method for the rapid and sensitive measurement of endonuclease activity comprising the following steps:

(a) providing nucleotide substrate target molecule having been synthesized to contain a specific hydrolysis site for the endonuclease of interest, with the target molecule being double-stranded with the exception of a single-stranded hydrolysis site, and with said target molecule being engineered to be non-complementary at the 3' end in order to prevent DNA polymerase extensions;

(b) introducing said target molecule to an endonuclease which will cleave the specific hydrolysis site of the phosphodiester backbone of the nucleotide substrate target molecule;

(c) after said hydrolysis of step (b) DNA polymerase with 5'→3' exonuclease activity is added in order to catalyze the extension of the 3' end of the cut DNA strand, and in addition the polymerase will also hydrolyze the cut strand in the region downstream of the endonuclease cleavage site, and after the cut strand has been extended along the entire length of the uncut strand, a template molecule for PCR is generated; and (d) performing a quantitative PCR assay to determine the amount of cleavage of the endonuclease of interest.

In the inventive method the hydrolysis cite for the endonuclease of interest is an Apurinic/Apyrimidinic site.

The inventive method can be described as a method for the rapid and sensitive measurement of endonuclease activity comprising the steps of:

(a) providing a synthetic nucleotide containing an Apurinic/Apyrimidinic site and reacting said site with an endonuclease to produce a cut strand of portions 5'→3' A and B and an uncut strand 3'→5';

(b) extending said A portion of 5'→3' polymer with DNA polymerase and destroying the B portion 5'→3' exonuclease activity of DNA polymerase; and (c) performing real-time PCR to determine endonuclease activity.

Advantages and Novel Features of the Invention

Nucleases take part in a variety of cellular events associated with the transfer and maintenance of genetic material. Due to their ability to recognize a wide variety of nucleic acid structures, considerable efforts have been made to evaluate the role of nucleases in different cellular processes as well as their application as analytical tools to study nucleic acids structure. Among them, the utility of single-strand-specific nucleases as analytical tools has been widely recognized and has led to their extensive application as probes for the determination of nucleic acid structure. A rapid screening assay to assess endonuclease activity would prove beneficial to the pharmaceutical industry as screening tool for assessing the activity of synthetic and natural enzyme preparations. An assay with increased sensitivity would enhance the capabilities of basic research attempting to identify and characterize new endonucleases. The herein disclosed invention accomplishes these objectives.

Agar plate method, zymogram analysis, Viscometry, Spectrophotometric analysis, and Atomic force microscopy are current techniques to assay endonuclease activity, but none of these methods posses the potential sensitivity of the above described technology.

Further Advantages to be Realized by the Invention

Enzymes that do not directly break the DNA backbone, such as some DNA glycosylases, can be analyzed using the technology of this invention, because the AP site generated by their action can be subsequently enzymatically cleaved by the addition of APE. As technology improves, the synthetic oligonucleotides used in this assay system can have far wider utility in drug screening, to which it can readily adapt for use in the analysis of other DNA enzymes that work in concert with APE such as those that unwind the DNA duplex. In addition, any enzyme or chemical that is able to cleave the substrate oligonucleotide backbone may also be assessed with this method.

DNA repair is also vital for the survival and propagation of bacterial pathogens. Bacteria undergo frequent replication, providing the opportunity for rapid accumulation of potentially cytotoxic mutations. Bacteria are also subject to oxidative stress during pathogenesis and must overcome the devastating damage caused by the oxidative burst within phagocytic cells of the immune system. To date, there have been few studies that have examined the role of base excision repair during pathogenesis despite its importance in maintenance of DNA integrity in the face of the innate host response to infection.

The technique of this invention may have a role in cancer research. Several preclinical and clinical studies have indicated that APE1 may be an attractive target for anticancer drug development. Depletion of intracellular APE1 sensitizes human cells to a variety of cytotoxic agents. Using either an antisense oligonucleotide or RNA interference approaches, several groups have reported that APE1 down-regulation confers sensitivity to mono-functional alkylating agents such as methylmethane sulfonate (MMS) and oxidizing agents such as hydrogen peroxide. APE1 function may also be related to the pathogenesis of several human cancers, and its expression may have prognostic and/or predictive significance. For example, APE1 is over-expressed in several human tumors and its expression pattern appears to have prognostic significance in cancers of the breast, lung and bone. In cervical cancers, increased APE1 expression has been shown to be associated with radiation treatment resistance, and a high level of nuclear APE1 was shown to correlate with resistance to chemotherapy and poor overall survival in patients with head and neck cancer. Given this evidence, APE1 inhibition may prove an important factor in a cancer treatment regimen, a drug screening technique may have great utility.

Obviously, many modifications may be made without departing from the basic spirit of the present invention. Accordingly, it will be appreciated by those skilled in the art that, within the scope of the appended claims, the invention may be practiced other than has been specifically described herein.

What is claimed is:

1. A method for the rapid and sensitive measurement of endonuclease activity, comprising the steps of:
   (a) reacting endonuclease with a synthetic double-stranded oligonucleotide having first and second complementary strands, wherein said first strand is a substrate and comprises the sequence of SEQ ID: NO 1 and wherein said second strand is a template and comprises the sequence of SEQ ID: NO 2, wherein said first strand contains an apurinic/apyrimidinic site and said first and second strands have a terminal dideoxy cytosine to prevent DNA polymerase extension at its 3' end, to thereby subject the apurinic/apyrimidinic site to endonuclease hydrolysis, said hydrolysis cleaving said first strand producing a 5'→3' chain labeled A and a 5'→3' chain labeled B and leaving the complementary 3'→5' second strand uncut;
   (b) reacting the 5'→3' chain labeled A with DNA polymerase to form a complementary strand to the uncut 3'→5' second strand; and
   (c) subjecting the reaction product of step (b) to a polymerase chain reaction to detect the initial endonuclease activity.

2. The method of claim 1, wherein said apurinic/apyrimidinic site comprises a tetrahydrofuran abasic site analog.

* * * * *

SEQUENCE LISTING

<160> NUMBER OF SEQ ID NOS: 5

<210> SEQ ID NO 1
<211> LENGTH: 61
<212> TYPE: DNA
<213> ORGANISM: Artificial Sequence
<220> FEATURE:
<221> NAME/KEY: SITE
<222> LOCATION: (46)...(47)
<223> OTHER INFORMATION: Tetrahydrofuran is used to modify site 46 and
      47. Serves as substrate for APE. Substrate is a commercial
      product. The 3' end is modified by 3ddc/3' to prevent extension by
      DNA polymerase.Chemically Synthesized
<223> OTHER INFORMATION: Chemically Synthesized

<400> SEQUENCE: 1
ggggttttgg gttttttttaa ttttaggttg tggttgtggt tgtcgggacg tgttggtttt    60
t                                                                    61

<210> SEQ ID NO 2
<211> LENGTH: 88
<212> TYPE: DNA
<213> ORGANISM: Artificial Sequence
<220> FEATURE:
<223> OTHER INFORMATION: The 3' end is modified by 3ddc/3'.  The DNA is
      a commercial product. Template contains region complementary to
      substrate for APE
<223> OTHER INFORMATION: Chemically Synthesized

<400> SEQUENCE: 2 ctttcgacc tacgatacgc gatccagtgt tgtatggat cctagagtttt tccaacacgt      60 ctccgacaac cacaaccaca accatttt                                        88

<210> SEQ ID NO 3
<211> LENGTH: 25
<212> TYPE: DNA
<213> ORGANISM: Artificial Sequence
<220> FEATURE:
<223> OTHER INFORMATION: Sequence forward primer; commercial product
<223> OTHER INFORMATION: Chemically Synthesized

<400> SEQUENCE: 3
ggggttttgg gttttttttaa ttta                                           25

<210> SEQ ID NO 4
<211> LENGTH: 20
<212> TYPE: DNA
<213> ORGANISM: Artificial Sequence
<220> FEATURE:
<223> OTHER INFORMATION: Reverse primer; commercial product
<223> OTHER INFORMATION: Chemically Synthesized

<400> SEQUENCE: 4
catttcgacc tacgatacgc                                                 20

<210> SEQ ID NO 5
<211> LENGTH: 25
<212> TYPE: DNA
<213> ORGANISM: Artificial Sequence
<220> FEATURE:

-continued

```
<223> OTHER INFORMATION: Probe is a commercial product.  There is a FAM
      at the 5' end and a TAMRA at the 3'.
<223> OTHER INFORMATION: Chemically Synthesized

<400> SEQUENCE: 5
tccagtgttt gtatggatcc tgagt                                              25
```